US008083908B2

(12) United States Patent
Marton et al.

(10) Patent No.: US 8,083,908 B2
(45) Date of Patent: Dec. 27, 2011

(54) HIGH STRENGTH VACUUM DEPOSITED NITINOL ALLOY FILMS AND METHOD OF MAKING SAME

(75) Inventors: Denes Marton, San Antonio, TX (US); Christopher T. Boyle, Flushing, NY (US); Roger W. Wiseman, Bulverde, TX (US); Christopher E. Banas, Breckinridge, CO (US)

(73) Assignee: Advanced Bio Prosthetic Surfaces, Ltd., Dallas, TX (US)

( * ) Notice: Subject to any disclaimer, the term of this patent is extended or adjusted under 35 U.S.C. 154(b) by 13 days.

(21) Appl. No.: 11/875,629

(22) Filed: Oct. 19, 2007

(65) Prior Publication Data

US 2008/0171214 A1   Jul. 17, 2008

Related U.S. Application Data

(60) Division of application No. 10/211,489, filed on Aug. 2, 2002, now Pat. No. 7,335,426, which is a continuation-in-part of application No. 09/853,985, filed on May 11, 2001, now Pat. No. 6,849,085, which is a continuation-in-part of application No. 09/443,929, filed on Nov. 19, 1999, now Pat. No. 6,379,383.

(60) Provisional application No. 60/203,835, filed on May 12, 2000.

(51) Int. Cl.
*C23C 14/35* (2006.01)
(52) U.S. Cl. ............... 204/192.15; 204/192.12
(58) Field of Classification Search .............. 204/192.12, 204/192.15
See application file for complete search history.

(56) References Cited

U.S. PATENT DOCUMENTS

| | | | |
|---|---|---|---|
| 3,354,074 A | 11/1967 | Kay | 204/298 |
| 4,419,202 A * | 12/1983 | Gibson | 204/192.16 |
| 4,569,745 A * | 2/1986 | Nagashima | 204/298.12 |
| 5,061,914 A | 10/1991 | Busch et al. | 337/140 |
| 5,084,151 A | 1/1992 | Vallana et al. | 204/192.11 |
| 5,133,845 A | 7/1992 | Vallana et al. | 204/192.15 |
| 5,358,615 A | 10/1994 | Grant et al. | 204/192.15 |
| 5,370,684 A | 12/1994 | Vallana et al. | 623/1 |
| 5,597,458 A | 1/1997 | Sanchez, Jr. | 204/192.3 |
| 5,624,508 A | 4/1997 | Flomenblit et al. | 148/510 |

(Continued)

FOREIGN PATENT DOCUMENTS

CA   2616781   5/2001

(Continued)

OTHER PUBLICATIONS

"Biocompatability Evaluation of Nickel-Titanium Shape Memory Metal Alloy" (Academic Dissertation) by Jorma Ryhanen, *University Hospital of Oulu*, pp. 1-117 (May 7, 1999).

(Continued)

*Primary Examiner* — Rodney McDonald
(74) *Attorney, Agent, or Firm* — Rosenbaum & Silvert, P.C.

(57) ABSTRACT

A vacuum deposition method for fabricating high-strength nitinol films by sputter depositing nickel and titanium from a heated sputtering target, and controlling the sputter deposition process parameters in order to create high-strength nitinol films that exhibit shape memory and/or superelastic properties without the need for precipitation annealing to attenuate the transition conditions of the deposited material. A vacuum deposited nitinol film having high-strength properties equal to or better than wrought nitinol films and which are characterized by having non-columnar crystal grain structures.

20 Claims, 9 Drawing Sheets

U.S. PATENT DOCUMENTS

| | | | | |
|---|---|---|---|---|
| 5,744,515 | A | 4/1998 | Clapper | 523/113 |
| 5,858,566 | A | 1/1999 | Zhang | 428/694 |
| 5,932,036 | A | 8/1999 | Fukai | 148/670 |
| 5,954,724 | A | 9/1999 | Davidson | 606/76 |
| 6,103,320 | A | 8/2000 | Matsumoto et al. | 427/535 |
| 6,113,750 | A | 9/2000 | Shinmura et al. | 204/192.2 |
| 6,126,761 | A | 10/2000 | DeHaven et al. | 148/518 |
| 6,149,742 | A | 11/2000 | Carpenter et al. | 148/563 |
| 6,358,380 | B1 | 3/2002 | Mann et al. | 204/192.2 |
| 6,402,906 | B1 | 6/2002 | Pichulo et al. | 204/192.15 |
| 6,428,569 | B1 | 8/2002 | Brown | 623/1.15 |
| 6,454,913 | B1 | 9/2002 | Rasmussen et al. | 204/192.15 |
| 6,689,486 | B2 | 2/2004 | Ho et al. | 428/610 |
| 2001/0001834 | A1* | 5/2001 | Palmaz et al. | 623/1.15 |
| 2001/0039449 | A1 | 11/2001 | Johnson et al. | 623/204 |
| 2002/0043456 | A1 | 4/2002 | Ho et al. | 204/192.1 |
| 2002/0125208 | A1 | 9/2002 | Christenson et al. | 216/2 |
| 2003/0018381 | A1 | 1/2003 | Whitcher et al. | 623/1.15 |

FOREIGN PATENT DOCUMENTS

| | | |
|---|---|---|
| CA | 2408801 | 11/2001 |
| EP | 1 224 989 | 7/2002 |
| EP | 1 131 018 | 9/2002 |
| JP | 7-90436 | 4/1995 |
| JP | 8-141068 | 6/1996 |
| WO | WO95/31945 | 11/1995 |
| WO | 99/16385 | 4/1999 |
| WO | 99/62432 | 12/1999 |
| WO | 01/21851 | 3/2001 |
| WO | 01/21852 | 3/2001 |
| WO | 01/55473 | 8/2001 |
| WO | 01/56502 | 8/2001 |
| WO | 01/70294 | 9/2001 |
| WO | 01/76525 | 10/2001 |
| WO | 01/82830 | 11/2001 |
| WO | 01/85064 | 11/2001 |
| WO | 01/04203 | 1/2002 |
| WO | 02/04197 | 1/2002 |
| WO | 02/04198 | 1/2002 |
| WO | 02/04199 | 1/2002 |
| WO | 02/04201 | 1/2002 |
| WO | 02/04823 | 1/2002 |

OTHER PUBLICATIONS

"Sputter deposition of NiTi thin film exhibiting the SME at room temperatures" by K. Ho, G.P. Carman and P. Jardine, *Mechanical & Aerospace Engineering*, UCLA, 38-137m Engineering IV, pp. 1-16.

"Modeling and Measuring the Response Times of Thin Film TiNi" by K. Ho, P. Jardine, G.P. Carman, and C.J. Kim, *Mechanical & Aerospace Engineering*, UCLA, 38-137m Engineering IV, pp. 1-15.

Abstract: "On the formation of nonequilibrium A15 crystal structure chromium thin films by sputter deposition" by J.P. Chu, et al., *Thin Solid Films*, vol. 312, Issues 1-2, pp. 78-85 (Jan. 14, 1998).

Abstract: "Microstructure and Properties of Cu-C Pseudoalloy Films Prepared by Sputter Deposition" by J.P. Chu, et al., *Metallurgical and Materials Transformations A*, vol. 29A, Issue 2, pp. 647-658 (Feb. 1998).

"Effects of thermomechanical history on the tensile behavior of Nitinol ribbon" by Cynthia L. Lach, et al., *SPIE's 9th Annual International Symposium on Smart Structures and Materials; Active Materials: Behavior and Mechanics*, vol. 4699, Paper No. 4699-45, pp. 17-21 (Mar. 2002).

"Ion Assisted Deposition of Crystalline TiNi Thin Films by Electron Cyclotron Resonance Plasma Enhanced Sputtering" by M. Misina, et al., *Jpn. J. Appl. Phys.*, vol. 36, Part 1, No. 6A, pp. 3629-3634 (Jun. 1997).

"Integrated Circuit-Based Fabrication Technologies and Materials", *Microelectromechical Systems: Advanced Materials and Fabrication Methods*, www.nap.edu/openbook/030905980/html/14.html (1997).

"Adhesion of Bovine Serum Albumin on Coated DLC (Diamond-Like) and Uncoated ($SiO_2$ / $TiO_2$) Sensor Chips", www.phytis.com/stent4.htm, pp. 1-2 Aug. 19, 1999.

"Gold-Coated NIR Stents in Porcine Coronary Arteries" by Elazer R. Edelman, et al., *Circulation*, pp. 429-434 (Jan. 23, 2001).

"Microdevice for Non-Invasive Control of Endothelial Cell Shape" by Bonnie L. Gray, et al., *BED*, vol. 50, 2001 Bioengineering Conference ASME, pp. 211-212 (2001).

"Our State of the Art Coating Technology: Ion Assisted Deposition (IAD)", www.bitstorm.net/graphics/coatings.htm, pp. 1-2.

"Sputter deposited NiTi thin film SMA for active flow control", by K. Ho, J. Gill and G. Caman, *Mechanical & Aerospace Engineering*, University of California, 38-'37m Engineering IV, pp. 1-12 (Oct. 1999).

"Composition Control of NiTi Shape Memory Alloy Films Formed by Sputter Deposition with a Composite Target" by F. Takeda, T. Yamazaki and T. Nakajima, *Jpn. J. Appl. Phys.*, vol. 39, Part 1, No. 10, pp. 5992-5994 (Oct. 2000).

Abstract: "Functionally Gradient NiTi Films Fabricated by Sputtering" by S. Takabayashi, et al., *Jpn. J. Appl. Phys.*, vol. 35, Part 1, No. 1A, pp. 200-204 (Jan. 15, 1996).

Abstract: "Dependence of Composition Distribution of NiTi Sputtered Films on Ar Gas Pressure", by T. Yamazaki, et al., *Jpn. J. Appl. Phys.*, vol. 40, Part 1, No. 12, pp. 6936-6940 (Dec. 15, 2001).

"Deposition and characterization of TiNi-base thin films by sputtering" by J.P. Chu, et al., *Materials Science and Engineering*, A277, pp. 11-17 (2000).

Abstract: "NiTi thin film characterization by Rutherford backscattering spectrometry" by F. Goldberg and E.J. Knystautas, *Materials Science and Engineering B.*, vol. 40, Issues 2-3, pp. 185-189 (Sep. 1996).

Abstract: "The time dependant, super-viscoelastic behavior of NiTi shape memory alloy fiber reinforced polymer matrix composites" by W. Armstrong and H. Lilholt, *Materials Science and Engineering B*, vol. 68, Issue 3, pp. 149-155 (Jan. 2000).

Abstract: "Thermoelectric triggering of phase transformations in Ni-Ti shape memory alloy" by P.L. Potapov, *Materials Science and Engineering B*, vol. 52, Issues 2-3, pp. 195-201 (Apr. 1998).

Abstract: "Effect of Aging on Shape Memory Behavior of Ti-51.3 At. Pct Ni Thin Films" by A. Ishida, et al., *Metallurgical and Materials Transactions A*, vol. 27A, Issue 12, pp. 3753-3759 (Dec. 1996).

Abstract: "Martensitic transformation in sputter-deposited Ti-Ni-Cu shape memory alloy thin films" by A. Miyazaki, T. Hashinaga and A. Ishida, *Thin Solid Films*, vols. 281-282, Issues 1-2, pp. 364-367 (Aug. 1996).

Abstract: "Transformations in sputter-deposited thin films of NiTi shape memory alloy" by Y.Q. Yang, et al., *Materials Letters*, vol. 22, Issues 3-4, pp. 137-140 (Feb. 1995).

Abstract: "Phase transformation of A15 crystal structure chromium thin films grown by the sputter deposition" by J.P. Chu, J.W. Chang, and P.Y. Lee, *Materials Chemistry and Physics*, vol. 50, Issue 1, pp. 31-36 (Aug. 1997).

"Modeling of Thermomechanical Response of Porous Shape Memory Alloys" by D. Lagoudas, et al., pp. 1-13.

"MEMS Thin Film Deposition Processes", by MEMSnet, www.memsnet.org/mems/beginner/deposition.html, pp. 1-8 (2001).

"Mechanical Behavior of Nanostructured Melt Spun NiTi Shape Memory Alloy" by D. Wu, W. Cron and J. Perepezko, *Society for Experimental Mechanics, 2002 SEM Annual Conference Proceedings*, pp. 1-4 (2002).

"Design and Fabrication of Shape Memory Alloy Actuated Titanium Matrix Composites", www.alroom.tutpse.tut.ac.jp/efpm/English/Research_subjects/Ti_intelligent.htm, pp. 1-9 (2002), Aug. 6, 2002.

"Micromechanics of Martensitic Transformation in Single and Poly-Crystals" by M. Berveiller, E. Patoor and M. Cherkaoui, www.newton.cam.ac.uk/programs/old_progs/SMM/bervieller.html, pp. 1-2 (2002), Aug. 6, 2002.

"Structural Mechanisms of High-Temperature Shape Changes in Titanium-Nickel Alloys After Low-Temperature Termomechanical Treatment" by S. D. Prokoshkin, et al., Canadian Metallurgical Quarterly, pp. 1-12, Aug. 6, 2002.

"Silicon bulk micromachining" by M. Esashi, www.//mems.mech/tohoku.ac.jp/esashilab/fsseminar/fsseminar.htm, pp. 1-23.

"Photolithographic Fine Patterning of Difficlut-to-Etch Metals" by John H. Glenn Research Center, www.nasatech.com/Briefs/Mar02/LEW17079.html, pp. 1-3, Sep. 25, 2002.

"Nano-Lithography of Metal Films Using AFM-Patterned Carbon Resist Masks" by G. Reiss, et al., Foresight Institute, www.foresight.org/Conferences/MNT6/Abstracts/Reiss/index.html, pp. 1-6 (Oct. 1998).

"A Temperature-Controlling Device for Refrigerators" by M.C. Shin, K.K. Jee and B.C. Ku, *Proceedings of the First International Conference on Shape Memory and Superelastic Technologies*, pp. 305-310 (1994).

"Nitinol melting, manufacture and fabrication" by D. Hodgson and S. Russell, *Min Invas Ther & Allied Technol*, vol. 9, No. 2, pp. 61-66 (2000).

"Growth and Erosion of Thin Solid Films" by G. Steven Bales, et al., *Science*, vol. 249, pp. 264-268, Jul. 20, 1990.

* cited by examiner

Ti$_3$Ni$_4$(100) very faint

HIGH STRENGTH VACUUM DEPOSITED NITINOL ALLOY FILMS AND METHOD OF MAKING SAME

CROSS-REFERENCE TO RELATED INVENTION

This application is a divisional of U.S. patent application Ser. No. 10/211,489, filed Aug. 2, 2002, and which issued as U.S. Pat. No. 7,335,426 on Feb. 26, 2008 which is a continuation-in-part of U.S. patent application Ser. No. 09/853,985, filed May 11, 2001 and which issued as U.S. Pat. No. 6,849,085 on Feb. 1, 2005, which is a continuation-in-part of U.S. patent application Ser. No. 09/443,929, filed Nov. 19, 1999 and which issued as U.S. Pat. No. 6,379,383 on Apr. 30, 2002 and claims priority from U.S. Provisional Patent Application Ser. No. 60/203,835, filed May 12, 2000; and is related to U.S. patent application Ser. No. 09/532,164 filed Mar. 20, 2000 and which issued as U.S. Pat. No. 6,537,310 on Mar. 25, 2003, which is also a continuation-in-part of U.S. patent application Ser. No. 09/443,929, filed Nov. 11, 1999 and which issued as U.S. Pat. No. 6,379,383 on Apr. 30, 2002.

BACKGROUND OF THE INVENTION

The present invention relates generally to shape memory and superelastic alloys and vacuum deposited metallic materials. More specifically, the present invention relates to nickel-based and titanium-based alloys fabricated by vacuum deposition technologies and which exhibit shape memory effect (SME) and/or superelastic behavior. The present invention also relates to a method of physical vapor deposition (PVD) of nickel-titanium alloys by sputter deposition in which several process parameters are controlled to achieve the inventive high-strength deposited nitinol films. It has been found desirable control the energy of particles emitted from the target as they arrive at the substrate surface. One process parameter, in particular, that has been found to contribute significantly to producing the inventive high-strength nitinol films is the mean free path of particles emitted during sputtering of the sputter deposition target must be greater than about one-half the distance of the spatial separation between the target and the substrate. This condition is set by the requirement that the kinetic energy of the particles that are deposited must be much greater than the thermal energy in order to promote non-columnar film growth. This condition of the arrival of energetic particles to the substrate can be fulfilled also in other deposition methods, such as ion beam deposition and laser ablation, for example, hence the inventive method can be practiced by using other methods than sputtering. Control of other deposition process parameters has also been found to influence the strength characteristics of the resulting deposited film, including, employing a hollow cathode dc magnetron, controlled heating of the target, controlling the base pressure and working gas quality to avoid oxygen contamination of the depositing film, controlling the deposition pressure, controlling the surface roughness of the deposition substrate, controlling the composition of the substrate to avoid diffusion contamination into the depositing nitinol, and applying a negative bias voltage to the substrate.

In the metallurgic arts, it is known that nickel-titanium alloys having nearly stoichiometric 50-50 atomic percent nickel and titanium exhibit SME and are superelastic above certain temperatures. It is also known that ternary alloys that contain mostly nickel and titanium but also contain other components such as copper, chromium, tantalum, zirconium, or other metals also often exhibit SME. Similarly, nickel and titanium-based quaternary or more complex alloys can exhibit the SME. As used in the art, and as used in this application, the term "nickel-titanium alloy" is intended to include binary, ternary and quaternary alloys containing nickel and titanium that exhibit shape memory effect.

SME nitinol alloys may be manufactured both by conventional metallurgy and by vacuum deposition (See U.S. Pat. No. 5,061,914). It has been found that vacuum deposition fabrication offers the possible advantage of readily adding alloying elements to produce a large variety of alloy films having a wide variety of transition temperatures. Heretofore, however, vacuum deposited films have exhibited inferior mechanical properties when compared with similar articles fabricated by conventional metallurgy. For purposes of this application, those materials fabricated by conventional metallurgical methods will be referred to as "wrought nitinol" or "wrought nickel-titanium alloys." This difference in mechanical properties between wrought nitinol materials and vacuum deposited nitinol materials significantly limits the usefulness of vacuum deposited nitinol films. Some of the most appealing potential applications of nitinol films include micro-electro-mechanical (MEMS) devices and medical devices, such as endoluminal stents. However, since its inception over ten years ago, virtually no vacuum deposited thin film nitinol devices have been commercially marketed because of their insufficient strength relative to similar devices fabricated from wrought nitinol.

Shape memory and superelastic nitinol materials undergo a reversible phase transition between martensitic (M) and austenitic (A) phases. It is this property that makes use of nitinol materials especially desirable in certain applications, including medical devices, microelectronic sensor devices or the like. The M phase is stable at lower temperatures and/or high stresses, and the A phase is stable at higher temperatures and/or lower stresses. One of the most important characteristics of nitinol is the M to A transition temperature. This transition occurs within a range between $A_s$ (start) and $A_f$ (finish). The transition process is endothermic and may be characterized by the heat effect, $\Delta H$ and by the $A_p$ temperature where, for a given rate of heating, the transition heat effect is maximum.

Wrought nitinol is produced by vacuum melting ingots. This method results in a nitinol material having the same transition temperature as the nitinol ingot, termed the "ingot $A_p$." The ingot $A_p$ depends on the stoichiometry of nickel and titanium and the ingot, and may be between −50° C. 100° C. The ingot $A_p$ is lower where there is excess nickel, i.e., greater than 50 at. %, and higher when the alloy contains excess titanium, i.e., more than 50 at. % Ti. Ingots are processed by shaping into sheets or tubes for further use in the industries such as the medical device industry. Particular end applications of nitinol materials require particular transition temperature values. However, ingots with a range of different $A_p$ values are not available for each application. In order to address this difficulty in available ingots, a method called precipitation annealing is employed in order to adjust the $A_p$ value of a given product.

Precipitation annealing typically involves annealing nitinol at temperatures between 200-500° C. for 10-180 min., then allowing the material to cool at a controlled cooling rate or by quenching at a temperature below about 200° C. As a result of precipitation annealing, the excess component in the ingot, either Ni or Ti, will precipitate out from the crystal structure and form inclusions such as, for example, $Ni_3Ti_2$, $NiTi_2$, or the like. These inclusions constitute a separate phase along the nitinol grain boundaries or within the nitinol grains and are termed "precipitates."

The degree to which precipitate formation is necessary depends upon the relationship between the ingot $A_p$ and the desired device $A_p$. Currently, manufacturer of a particular nitinol device, such a medical device manufacturer, e.g., a stent manufacturer, will purchase raw material, such as sheets or tubes from an nitinol ingot fabricator. The ingots from which the raw material is fabricated, will, in all likelihood vary in their material constitution and $A_p$ value during the life of the device manufacturer's product line. Thus, in order to achieve a desired device $A_p$, device manufacturers must adjust the precipitation-annealing step for the given ingot $A_p$ of any particular batch of raw material received from the ingot fabricator. The inevitable result of this need to engage in precipitation annealing to adjust for the ingot $A_p$ is that there is variability in the amount of precipitates within the same device product line depending on the starting raw material. Because control of the ingot $A_p$ values ingot to ingot is extremely difficult, this variability is present even where ingots are made by the same fabricator.

Precipitates in metals have implications for the mechanical, corrosion, and fatigue properties. Precipitates tend to constrain slip plane movements during plastic deformation and hence the concept of precipitation hardening of metals. Hardening, if it is desirable, can also be achieved using cold working in traditional metallurgy. In the case of thin film metallurgy, hardening may be controlled by the deposition parameters through controlling grain size, which is a function of substrate temperature and growth rate, among others. So, even if hardening is desirable, it can be achieved by alternative methods, without resorting to induced precipitate formation. Concerning other mechanical properties, precipitates tend to make materials more brittle, and decrease fatigue life. This is caused by local strain fields that arise around the precipitates, which are situated incongruently between the grains of the material. Precipitates may initiate micro-cracks along the grain boundaries and are known to contribute to intergranular failure. With regard to corrosion properties, precipitates may have detrimental effects in two ways: (i) the mentioned strain field and the related micro-cracks may increase the effective surface area exposed to corrosive environment and (ii) local micro-elements (corrosion pairs) may be formed by the precipitate and the surrounding nitinol matrix.

It is known that nitinol can be made not only using the traditional metallurgical approach described in the previous paragraphs but also using film deposition technologies. Inherent in this approach, the producer of nitinol can have as good or better a control of the $A_p$ transition temperature than in the production of ingots. Deposition can provide fine adjustment of the nitinol chemical composition and thus to eliminate or reduce precipitation thereby reducing hardness, and consequently reducing the plateau stress, and improving the strength at the same time. However, deposition technologies are not commonly used in applications where the composition control must be within about 0.1 at % in order to control the transition temperature within about 10° C.

The most common deposition method for producing nitinol is dc sputter deposition. We will describe the invention in terms of a distinct form of dc sputter deposition, i.e., using the example of hollow cathode (HC) dc magnetron sputtering (See, e.g., E. Kay, Cylindrical Cathode Sputtering Apparatus Including Means for Establishing a Quadrupole Magnetic Field Transverse of the Discharge, U.S. Pat. No. 3,354,074, Sep. 16, 1963). However, the skilled in the deposition art will see that the principles outlined are applicable for a wide range of deposition methods.

Typically, sputter deposited nitinol is more Ni-rich than the sputtering target employed. The reasons for this are complex and without a good understanding of these reasons, various researchers have employed a variety of remedies. These include (i) the addition of extra Ti to the target in form of Ti sheets placed on the target, or some similar approach, and (ii) allowing the target to reach high temperatures, whereby, as experience shows, the Ti content of the films is enhanced. It is an object of the present invention to provide a method of adjusting the Ti content (Ni to Ti atomic ratio) of deposited nitinol films using the above and the adjustment of sputtering parameters.

Vacuum deposition of nitinol provides the additional advantage over wrought nitinol in that high Ni content material can easily be produced. The manufacturing of high Ni content wrought material is impeded by its extreme abrasiveness and toughness that makes extrusion, rolling and the like not feasible. In particular, the production of devices from wrought nitinol with $A_p < -20°$ C. is very difficult if not impossible. (See, e.g., D. Hodgson and S. Russell: "Nitinol melting, manufacture and fabrication" in Minimally Invasive Therapy & Allied Technologies, Vol. 9 No 2 March 2000 pp 61-65). Further advantages of vacuum deposition include (1) the ability of making thin walled tubes with high wall thickness uniformity, (2) the ability of making thin sheets with high thickness uniformity, (3) the ability of making objects with complex shapes, for example tubes with variable diameter along the length, such as funnel and balloon shapes, (4) better control over the material purity (5) control over material composition in terms of adding minor alloying elements such as, for example Ta in order to improve radio opacity.

Typically, sputter deposited nitinol has inferior mechanical properties as compared to wrought nitinol. This inferiority is manifest most clearly in the ultimate strength. The ultimate strength of the nitinol material described by Johnson (A. D. Johnson et al. US Patent Application 2001/0039449) appears from FIG. 3 in the published application to be approximately 500 MPa.

Mechanical properties of metals typically depend on their microstructure. Specifically, microstructure of deposited metal films consists of two main types of features: (i) the grain structure with the grain boundaries and precipitates both intragranular and intergranular, and (ii) texture such as columns. The grain structure is important because it determines the fundamental mechanical properties. Amorphous metals, i.e., those metals having no defined grain structures or grains that are too small to be detected by X-ray diffraction, are known to be very hard and brittle. Similarly, crystalline metals having very small grain sizes are also known to be quite brittle, but become more ductile as the grain size increases. When the grain size becomes very large, the metals lack strength and have low elastic limits. Thus, achieving a correct grain size plays a significant aspect of any metal fabrication technology. It is known that for wrought nitinol materials it is desirable to have grain sizes typically within the range of 0.1-10 μm in order to have practical mechanical properties.

In order to deposit nitinol films having thicknesses on the order of 0.1-25 μm, high deposition rates are typically employed. At such higher deposition rates, the resultant nitinol film develops generally columnar grain morphology. This columnar morphology is significant because it imparts features similar to grain boundaries, yet the columnar features traverse substantially the entire thickness of the resulting film. Like typical grain boundaries, the columnar grain morphology creates defect regions that are weaker than other regions of the film, and contaminants and precipitates may segregate into these defect regions. It is necessary, therefore, to avoid columnar grain growth during vacuum deposition in order to obtain nitinol films with higher mechanical strengths. Columnar growth results from the combination of the following factors: (i) low surface diffusion rate, (ii) expressed surface features, such as roughness, and (iii) directional deposition See, e.g., G. S. Bales, R. Bruinsma, E. A. Eklund, R. P. U. Karunasiri, J. Rudnick, A. Zangwill, *Growth and Erosion of Thin Solid Films*, Science, Vol. 249 p. 264-268, July 1990). It is an object of this invention to provide a method of choosing deposition parameters that result in nitinol film growth process without columnar growth.

SUMMARY OF THE INVENTION

In accordance with the method and material of the present invention vacuum deposited nitinol films having grain sizes within the range of 0.1-1 μm have been produced and exhibit optimal mechanical properties. Thin walled nitinol tubes, such as tubes with diameters in the 1-16 mm range have been successfully manufactured using the inventive technology with wall thicknesses of about 3-20 micron with wall thickness uniformity of about <10%. Sheets have been formed from tubes by cutting along the longitudinal axis of the tube, however, such sheets are readily fabricated in planar vacuum deposition systems. Prototype angioplasty balloons capable of being repeatedly inflated at pressures of several Atm have also been fabricated using the inventive methodology. The method of the present invention avoids using lubricants necessary in fabrication using cold working processes that contaminate heavily cold worked materials such as small diameter tubes like those used for cutting coronary stents. Finally, nitinol tubes having about 5% Ta added have been produced using the inventive method.

It is a principle objective of the present invention to provide high strength deposited nitinol materials. In particular, it is an object of the present invention to provide high strength vacuum deposited nitinol films that are useful in medical, mechanical and electronic applications. A further objective of the present invention is to provide a method of making the high strength nitinol materials. Additionally, in view of the difficulties in maintaining desired $A_p$ values, the present invention provides a method of forming nitinol materials having desired transition temperature values without employing precipitation annealing.

The present invention provides high strength nitinol materials that may be used either as precursors or finished products with improved mechanical strength, fatigue and corrosion resistance when compared to wrought nitinol materials. The inventive vacuum deposition process is essentially a vacuum deposition process in which Ni and Ti atoms are co-deposited from a target or targets onto a substrate where they form nitinol alloy. The inventive process is carried out with control over the atomic ratio of the resulting nitinol film, such that no precipitation annealing is required in order to tailor or adjust the $A_p$ transition temperature of the deposited film. The individual details of the inventive deposition process, including the fabrication of the nitinol target, the target temperature, the substrate surface roughness, application of a voltage bias, and other deposition parameters are chosen such that the resulting nitinol film has the chemical purity and crystalline microstructure necessary to produce high mechanical strength.

The method of the present invention entails vacuum depositing under conditions where the sputtering target and substrate are spatially separated from one another such that the mean free paths of the particles emitted from the target is greater than about half the distance between the target and the substrate. According to the best mode known at the present time to the inventors, vacuum deposition is conducted in a hollow cathode dc magnetron, in which the sputtering target is partially or fully thermally decoupled or insulated from a cooled cathode in the sputtering reactor. The target temperature is regulated by the applied sputtering power. The target composition is selected according to the desired transition temperature and the nitinol target may be modified by adjusting the relative amounts of Ni or Ti in the target by welding Ni or Ti wires to the target surface. Alternatively, separate Ni and Ti targets may be employed, with the ratio of Ni target to Ti target being adjusted to achieve the desired transition temperature in the deposited nitinol film. The applied sputtering power is chosen such that the target temperature is high enough to produce a desired amount of Ti segregation, as determined from the Ti content of the resulting nitinol films. The base pressure and Ar gas quality are selected to avoid oxygen contamination of the nitinol film. The deposition pressure and the target-to-substrate distance, also known as the "throw distance" are sufficiently small to minimize atomic scattering of the Ni and Ti atoms within the plasma. Additionally, the surface roughness of the substrate is controlled so that it is substantially uniformly smooth. Additionally, the substrate temperature is selected to be sufficiently high so that at a given selected deposition rate the deposited nitinol material will be crystalline. The substrate temperature is preferably balanced to also be sufficiently low in order to avoid diffusion contamination from the substrate into the deposited nitinol. The substrate is preferably negatively biased to a bias voltage selected to be sufficiently high in order to atomically compact the deposited nitinol film, yet sufficiently low in order to avoid substantial deleterious effects such as re-sputtering from the substrate or Ar implantation.

Thus, by stringently controlling the parameters of sputter deposition, the method of the present invention achieves a balance of process parameters that yield a nitinol film having improved strength and predictable and defined $A_p$ values without the need for precipitation annealing to adjust or attenuate the transition temperature of the finished nitinol material.

BRIEF DESCRIPTION OF THE FIGURES

FIG. 12 (Section b) is a dark field optical micrograph taken through a 100× objective of a 5 μm nitinol film grown under conditions where energetic particles from the target were admitted to the substrate.

DETAILED DESCRIPTION OF THE PREFERRED EMBODIMENTS

The present invention includes an inventive high-strength shape memory and/or superelastic nitinol material as well as a process for fabricating the inventive material. The inventive material is characterized by having high mechanical strength and toughness. In accordance with the method of the present invention, the inventive high-strength nitinol material may be produced for certain intended end-uses, such as MEMS and medical devices, using deposition technologies including but not limited to PVD, sputter deposition, plasma deposition, ion beam deposition or the like to form the film, and post-deposition use of etching, photolithography, machining, or ablation techniques to fashion the deposited film for an intended end-use.

By employing vacuum deposition methodologies, one is able to form materials directly into a desired 2D or 3D geometry, e.g., planar, tubular, or multi-surfaced geometries. The common principle of the deposition processes is to take a material in a minimally processed form, such as pellets or thick foils (the source material) and atomize them. The term atomization is used here loosely to include forming atomic or molecular size particles, both charged and/or neutral and both comprised of a single atom and/or of a cluster of atoms. Atomization may be carried out using heat, as is the case in PVD, or using the effect of collisional processes, as in the case of sputter deposition, for example. The atoms or particles of the source material then deposit on a substrate or mandrel to form the desired material. In most cases, the deposited material is then either partially or completely removed from the substrate, to form the desired product.

Without limiting the scope of application of the present invention, the following are specific examples of products or devices which may be fabricated using the present invention: implantable nitinol stents, nitinol grafts, stent-graft devices in which either or both components are fabricated from the inventive nitinol material, general purpose seamless nitinol tubes, sheets, films or foils which may be, for example, employed as MEMs devices.

Figure 2:
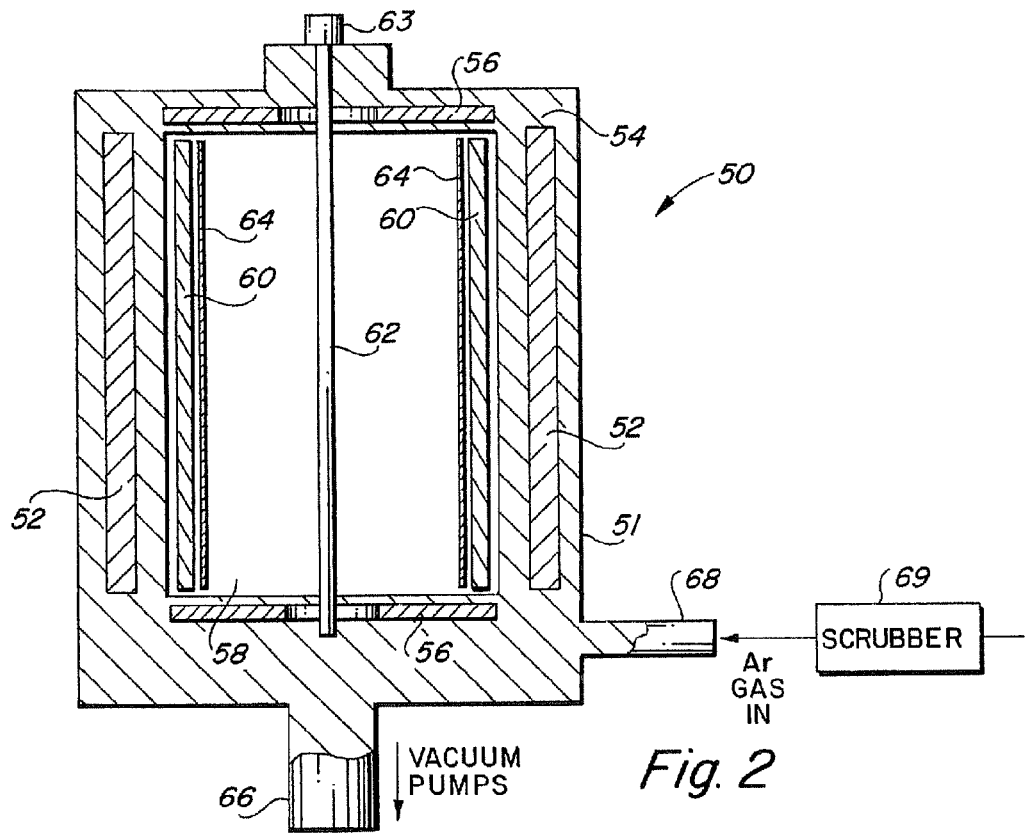
FIG. 2 is a diagrammatic representation of the inventive cylindrical magnetron sputtering apparatus.

As an aid to understanding the present invention, FIG. 2 provides a diagrammatic view of a vacuum sputter deposition system 50 useful in practicing the inventive methodology. In deposition system 50 there is provided an exterior housing 54, a cooling jacket 52 in thermal contact with the hollow cathode 60, a cylindrical target 64, a substrate 62 positioned along the central axis of the system 50, and a rotary motor 63 coupled to the substrate 62 for providing rotational motion to the substrate within the system 50. Seals 56 serve to isolate deposition chamber 58 from the ambient environment. A gas feed input port 68 permits the introduction of argon gas into the deposition chamber 58, while a vacuum port 66 permits communication between the deposition chamber 58 and vacuum pumps to obtain a vacuum within the deposition chamber 58. A scrubber 69 is preferably placed upstream to and in line with the gas feed input port 68 in order to provide purify the working gas of contaminants, particularly oxygen or nitrogen that may be present in the gas.

It has been found that the resultant strength of a vacuum deposited nitinol material is dependent entirely upon the target composition and the process parameters employed during vacuum deposition. In accordance with the present invention, it has been found desirable to achieve a balance of a multiple number of process parameters, each of which influence the resulting mechanical and physical properties of the resulting nitinol material.

In accordance with the best mode contemplated for the present invention, during deposition, the deposition parameters are controlled to optimize deposition of nitinol onto the substrate. Specific definition of the sputtering process includes the detailed geometry of the sputtering device including the magnetic field strength and distribution. In the case of hollow cathode dc sputter deposition, the sputtering parameters include but are not limited to the following: the base pressure of the vacuum system, the quality and pressure of the process gas, the quality and finish of the substrate material, the temperature of the substrate, the power and voltage supplied to the cathode, the material quality of the target or targets, the target surface temperature, and the throw distance. A judicious choice of these parameters enables one to produce high-strength vacuum deposited shape memory materials with the required microstructure and the proper chemical composition to control $A_p$, without the need for precipitation annealing.

The rate of film growth is another significant parameter of deposition processes. In order to deposit materials that are sufficiently thick so that they can be compared in functionality with wrought metal products, deposition rates in the order of 1 μm/hour or higher are desirable. Depending on other deposition parameters, and most importantly on the substrate temperature in vacuum deposition methods, the structure of the deposit may be amorphous or crystalline. When hollow cathode dc sputtering techniques are employed, a high strength 5 μm thick nitinol film may be deposited in about less than one hour.

In accordance with the method of the present invention, the inventive material is made by positioning a cylindrical deoxygenated copper mandrel along the axis of a cylindrical hollow cathode dc magnetron sputtering device. The sputtering target is formed from a nitinol sheet that has a thickness of about between 1 and 3 mm. The target is formed into a cylindrical shape so that it forms a continuous cylindrical surface. In accordance with a preferred embodiment of the invention, the target is made of nitinol sheet with either Ni or Ti added in form of spot welded wires to the working target surface. The transition temperature of the deposited film may be shifted to lower values by the addition of Ni wire, whereas the transition temperature may be shifted to higher values by the addition of Ti wire. Alternatively, the target may be made of either a titanium or nickel sheet or tube and either nickel or titanium pieces, respectively, bound to the surface of the sheet or tube, such as by welding. Finally, minor alloying components, such as tantalum, may be added to the target by affixing wires or sheets of the alloying component to the target. The target is placed inside the cathode and electrical contact is made between the cathode body and the target.

It is known and well accepted in the conventional methods of sputter deposition to maintain thermal contact between the cathode and target such that the cathode cooling jacket act to dissipate heat from both the target and the cathode, thereby cooling the target. Usually, the cathode is cooled using water circulation or sometimes using Peltier cooling elements. However, in a departure from these conventional methods of magnetron sputtering, and in accordance with one preferred embodiment of the present invention, the thermal contact between the cathode and the target is intentionally reduced. While cathode cooling is maintained in order to protect the magnets of the magnetron from overheating, the thermal contact between the cathode and the target is reduced or substantially eliminated.

Thermal isolation of the target from the cathode is achieved by interposing a thermally insulating or dielectric material between the cathode and target. In one embodiment, this material may be a ceramic cylinder; in an alternative embodiment, it may be a set of thin thermally conductive spacers, such as metal, that reduce the heat conductivity between the cathode and target may be employed to reduce the cooling of the target and permit target heating, but to a lesser degree that where the target is thermally isolated from the cathode cooling jacket.

Alternatively, in accordance with another preferred embodiment of the invention, the target may be in full thermal contact with the cathode. In this embodiment the thermal contact between the target and the cathode is unchanged from conventional sputter deposition methodologies and no reduction in thermal coupling is employed. However, in order to adjust for the cooler target surface conditions, other sputter deposition process parameters are adjusted, such as the magnetic field strength, the working gas pressure, the target-substrate throw distance, the sputtering power and/or the cathode voltage are adjusted in order to maintain sufficient energy being applied to the target species to ensure adequate energies of the species arriving at the substrate surface.

It is known in the vacuum deposition arts that sputtering is best carried out in vacuum systems with the base pressure in the high vacuum range, i.e. about in the $10^{-6}$-$10^{-7}$ Torr range, or better. The working gas pressure during the deposition is typically between about 0.1 mTorr and 30 mTorr. While the working gas is preferably argon, alternative gases such as from He, Ne, Kr, or Xe may be employed. At a normal purity level of 99.999% for high purity Ar, the total partial pressure of the contaminants at less than about 30 mTorr working pressure is less than about $3 \times 10^{-7}$ Torr, which is typically considered acceptable for sputter deposition.

In a departure from this conventional practice, in accordance with the best mode of the inventive process includes additional steps are employed to reduce the impurity levels of the working gas. In order to reduce the impurity level of the argon working gas, a scrubber is added to the argon gas line to reduce oxygen in the argon input feed line. The scrubber employs heated titanium that oxidizes to titanium oxide and captures contaminating oxygen in the argon feed line. Additionally, in accordance with the best mode of the inventive method it is desirable to include a titanium sublimation pumping system to reduce the $O_2$ partial pressure in the working gas during the deposition. While the foregoing steps have been employed in accordance with the method of the present invention, those of ordinary skill in the vacuum deposition arts will understand that alternative methods for removing impurities in the gas feed and to reduce the oxygen background pressure may be employed.

Figure 1:
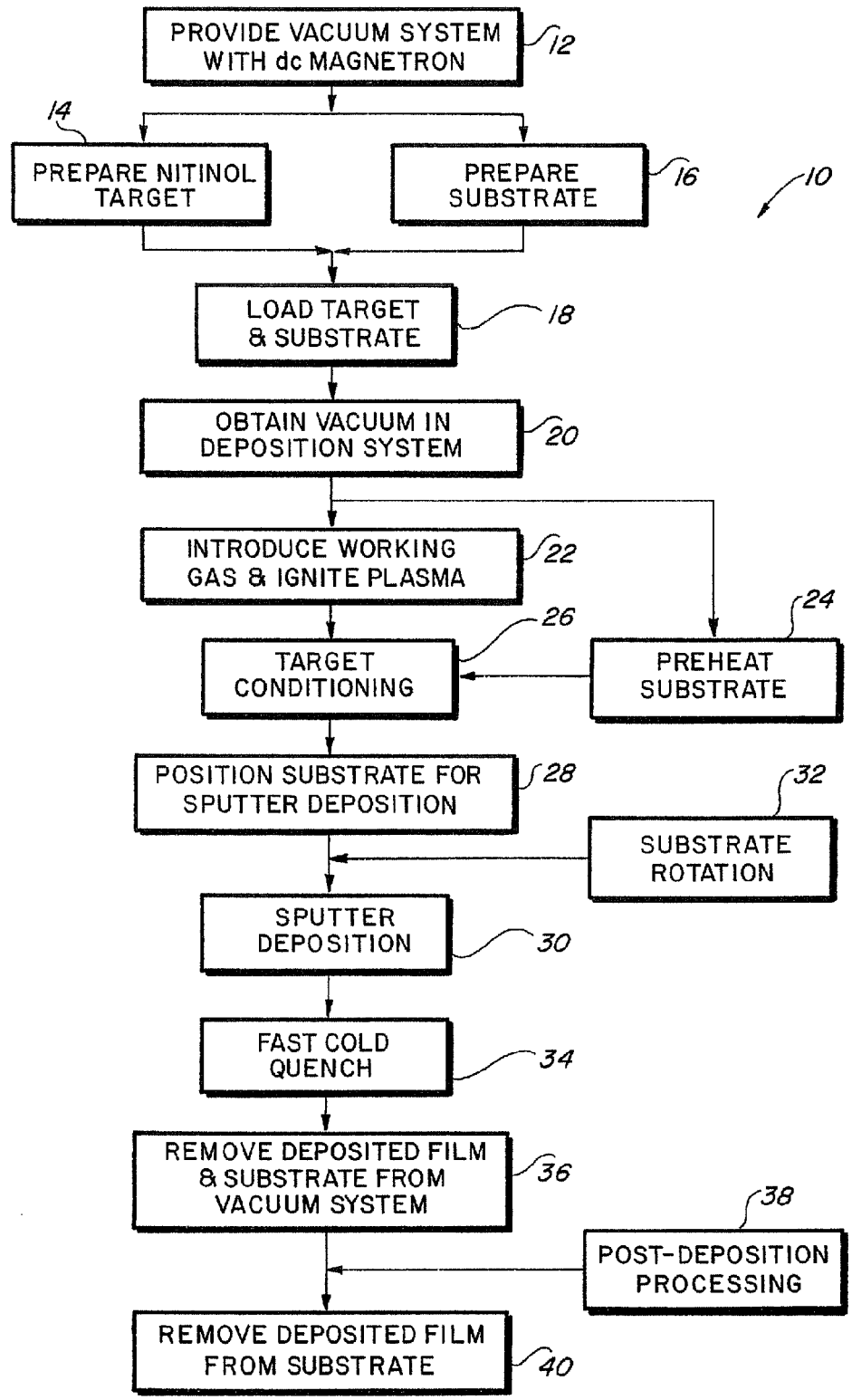
FIG. 1 is a process flow diagram of inventive method for fabricating high-strength nitinol films.

As illustrated in FIG. 1, the inventive method 10 generally comprises the steps of providing a deposition reactor having a vacuum system and dc magnetron 12, providing and preparing a target 14 and a substrate 16, loading the target and substrate into the reactor 18, then obtaining a vacuum in the reactor 20. Argon working gas is introduced into the reactor and a plasma is ignited 22, the target is conditioned 26 and the substrate preheated 24. It is preferable to condition or clean the surface of the nitinol target prior to deposition the first time by creating plasma within the chamber and exposing the target to the plasma for a period of several hours. After the first use and prior additional uses, the target is conditioned for a shorter period of time (for example, for 30 min), such that is sufficient for the plasma process to reach steady state. After the substrate is pre-heated and the target is prepared, the substrate is positioned within the dc magnetron 28, and the sputter deposition process is initiated 30 by applying a voltage to the cathode. It has been found that negative bias voltage of between about 40 V and 120 V, preferably between 60 V and 100 V, is desirable in order to impart additional energy to the Ni and Ti atoms that arrive onto the substrate and form the deposited film. This additional energy through a "peening" effect results in high film density and stronger films. Where there is a cylindrical substrate, it is desirable to rotate the substrate 32 during the deposition run. Film deposition is preferably carried out at a rate of between about 2 and 10 μm per hour. After the deposition run, the deposited film is cold quenched 34 within the vacuum system, then removed from the vacuum system 36. In accordance with the invention, post-deposition processing of the deposited film may be employed while the film remains on the substrate 38. For example, laser or chemical etching of the deposited film may be employed in order to impart a desired geometric pattern to the film, or dimension the film for its intended use. Finally, the deposited film is removed from the substrate 40.

The power input from the dc magnetron power supply in combination with the power input from the biasing power supply result in energy being dissipated in the target, the plasma and the substrate. In addition, the substrate may be heated by a separate heat source. Normally, the cathode cooling would serve as a heat sink to dissipate heat from the target and cathode. However, because in the inventive sputtering method the thermal contact between the target and the cooling is attenuated or eliminated, the applied energy heats the target, the working gas, and the substrate. The heating effect may be controlled by adjusting the power input, the level of thermal coupling between the target and cathode, and/or by adjusting the thermal conductivity of the substrate holder.

The significance of the substrate temperature is well understood in the deposition arts. On relatively cooler substrates films growth is essentially amorphous, with grain size increasing with the substrate temperature. At lower substrate temperatures there is an increased tendency for columnar film growth.

We have recognized, however, that higher deposition temperatures may not be as significant in reducing columnar growth, as is the level of energy of the sputtered atoms arriving at the substrate surface. Apart from their effects on the resulting deposited material, the sputtering process itself is largely independent of the target and gas temperature. The elevated target temperature has greater significance where multicomponent targets are employed. With multicomponent targets, preferential sputtering of an individual component combined with radiation enhanced segregation and diffusion can take place. With nitinol, however, at low temperatures where the components are "frozen" and immobile, after initial transients the sputtering yields of Ni and Ti even out.

However, perfect reproduction of the target composition is typically not achieved in the deposited film. It is thought that two reasons exist for this phenomenon. First, the Ni and Ti atoms have to reach the substrate after traveling through the distance separating the target from the substrate, called the throw distance. Second, the angular distribution of the sputtered Ni and Ti atoms is different. Ni tends to have a lower ejection angle relative to the surface of the target, while Ti has a greater ejection angle and leaves the target surface at a higher angle of incidence relative to the target surface. This difference in ejection angle between nickel and titanium, results in a lower Ti content and in lateral inhomogeneity of the nitinol films.

In conventional planar sputtering equipment the throw distance is typically 2-6" or about 5 cm to 15 cm. The significance of the throw distance is that the Ni and Ti atoms have a chance to collide with the atoms of the working gas, scatter, and be either re-deposited on the target or be entirely lost from the deposition process by being deposited elsewhere. The longer the throw distance, and the higher the gas density, the bigger are the re-deposition effects and the losses. The scattering cross section is larger for the Ti atoms than for the Ni atoms and hence the tendency, under usual circumstances, of depositing films with higher Ni content. This effect is counteracted to some extent by the fact that the re-deposited material is preferentially sputtered. Common solution to this problem is to add extra Ti in the form of additional targets or target pieces. However, such solutions may lead to laterally inhomogeneous deposits and loss of the fine composition control that is required for the deposition of useful nitinol films. The atom scattering between the target and substrate results in Ti deficiency and in temporal inconsistency of the deposited nitinol composition because of the combination of the transient effects involved.

In contrast, at elevated temperatures the target surface composition is influenced by the segregation of Ti, i.e., there is an excess Ti concentration at the target surface. This leads to more Ti sputtered and Ti-enriched films produced. In addition, the target becomes slowly depleted in Ti. The control of the target temperature provides a fine control over the Ti content in the deposited nitinol. Depending on the desired transition temperature of the nitinol deposit, one can select the deposition power to optimize the target temperature for the required Ti segregation, and one may improve substrate cooling or introduce additional substrate heating in order to optimize the process.

The substrate temperature is preferably kept above 400° C. and, most preferably, is about 500° C. At these temperatures interdiffusion between the deposited nitinol and the typically oxygen-free Cu (OFE Cu) substrate material is negligible, yet the surface mobility of the deposit is sufficiently high in order to help to suppress columnar growth. Vacuum deposition onto a substrate that is not pre-heated is also contemplated by the present invention. By controlling the other process parameters, it is possible to impart sufficient energy to particles arriving at the surface of the substrate to suppress columnar growth and the inventive high-strength nitinol material may be fabricated without the need for substrate pre-heating.

In accordance with the present invention, it has been found preferable to have a throw distance less than about 2.5 cm. By employing a smaller throw distance and minimized Ar pressure relative to the conventional deposition processing, scattering of the Ni and Ti atoms during deposition is limited and an atomic concentration of Ni to Ti closer to that of the target is more readily achieved.

In addition to the above considerations, the throw distance, the pressure and temperature have an additional significance heretofore not sufficiently recognized. Under typical deposition conditions (Ar pressures and temperatures) used in the sputtering arts, the mean free path is in the mm range during the deposition process. The sputtered atoms leave the target surface with a few eV energy (the most probable value within a quasi Maxwellian distribution with a long high energy tail). Due to the fact that the typical throw distance is several cm, i.e., about an order of magnitude longer than the mean free path, the sputtered atoms typically suffer several collisions before they are deposited. As a result, they lose much of their initial kinetic energy, or thermalize. However, this energy plays an essential role in providing for crystalline film growth without columns. The combination of the deposition parameters described in the exemplary deposition process ensures that the throw distance and the mean free path are of comparable magnitude. Other sets of parameters may be able to provide for the same result and thus may achieve the same nitinol film properties as described herein.

Figure 11:
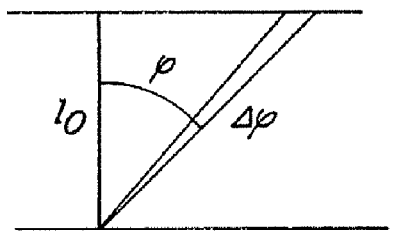
FIG. 11 is a graph depicting the average flight distance of an atom between coplanar surfaces of a target and a substrate.

The cylindrical magnetron geometry is essentially the same as having a large planar target and a large parallel planar substrate. Large is defined here as having large dimensions compared to the target to substrate distance. The distance between the target and the substrate is uniform in both cases. Assuming a cosinusoidal distribution of the sputtered particles, the real throw distance, i.e., the average flight distance between two planes (target and substrate) is illustrated with reference to FIG. 11. The geometric distance is $l_0$; a generic flight direction is at the angle $\phi$, at this direction the distance is l. Then the average is calculated as $$<l> = \int_{-\pi/2}^{\pi/2} f(\varphi) l(\varphi) d\varphi \quad (1)$$

where $$f(\varphi) = \frac{1 + \cos 2\varphi}{\pi} \quad (2)$$

is the distribution function. The evaluation of the integral yields $$<l> = 4l_0/\pi = 1.27 l_0. \quad (3)$$

The throw distance is somewhat higher for the Ti atoms than for the Ni atoms because, as experiments show, the Ni distribution is somewhat narrower than cosinusoidal (V. S. Chemysh, V. S. Tuboltsev, V. S. Kulikauskas "Angular distributions of Ni and Ti atoms sputtered from a NiTi alloy under He$^+$ and Ar$^+$ ion bombardment" *Nuclear Instruments and Methods in Physics Research B*, Vol. 140, 1998, pp. 303-310).

The mean free path (MFP) can be taken to be inversely proportional to the collisional cross section and hence proportional to the square root of the atomic mass:

$$\lambda \propto \sqrt{M} \quad (4)$$

Since the average atomic mass of Ni is 58.71 g/mol and the average atomic mass of Ti is 47.90 g/mol, the ratio of the MFPs is 1.11. Assuming that the effect on the composition is a result from collisional loss of Ti, the effect should be proportional to the average number of collisions on the way from the target to the substrate. This collision frequency can be estimated as the ratio of the throw distance and the MFP. It is difficult to accurately estimate the MFP but we can estimate it to be close to the Ar MFP and then modify it by the square root rule (4). At 10 mTorr the Ar MFP $\lambda$=4.9 mm. This is for 300K. At 800K (an estimated temperature of the working gas during deposition with a hot target), and taking into account that ions have MFPs √2 times of atoms, one obtains λ=18.5 mm. The collision frequency N can be estimated then as $$N = \frac{<l>}{\lambda} \qquad (5)$$

Then the effect on the composition can be estimated as $$\frac{C_{Ni}}{C_{Ti}} \propto \left(\sqrt{M_{Ni}/M_{Ti}}\right)^N \qquad (6)$$

This formula can be used to show that a 3 mm change in the target-substrate distance from 20 mm to 17 mm can result in 0.6-0.7 at % change in the Ti content and therefore in a 60-70° C. change in the transition temperature of the deposited film.

In accordance with the best mode known to the inventors, the inventive deposition process comprises generally the following steps:

a. A nitinol target is prepared such that it fits into the HC magnetron but the thermal contact between the water-cooled cathode and the target is interrupted by placing a thin ceramic cylinder between the cathode and the target;

b. Electrical contact is provided between the cathode and the target;

c. The substrate is oxygen-free (OFE) copper tube polished on its outside to a surface finish where the surface roughness is $R_a$<50 nm for a 500 μm long trace with a 100 μm low pass filter;

d. The substrate is placed in the deposition chamber which is subsequently pumped to a base pressure about <2×10$^{-7}$ Torr;

e. The substrate is preheated to a temperature between about 400° C.-500° C., alternatively, it is also contemplated that the substrate preheating step may be eliminated, and the deposition occur onto a non-preheated substrate surface;

f. Pure Ar gas (99.99% or purer) is admitted to the deposition chamber at a pressure between about 1 mTorr and 20 mTorr;

g. Target conditioning: The magnetron is powered up to produce plasma and is used for about 10-40 min with a dummy substrate to achieve stable deposition conditions. The magnetron power is about between 0.1 kW and 1 kW for a target size of about 50 mm diameter and about 150 mm length. The voltage on the cathode is maintained between about 400 V and 1000 V, preferably between 600-900 V, and is kept constant. The Ar gas feed is regulated to adjust the Ar gas pressure to maintain a constant cathode voltage;

h. The substrate is moved in the sputtering position which provides for a throw distance of about 10 mm to 25 mm, which is about equal on all sides;

i. The substrate is rotated along its longitudinal axis with a rotational velocity of about between 10 rpm and 200 rpm;

j. A negative bias voltage between about −60 V and −100 V is provided to the substrate;

k. The sputtering is carried out for a duration that provides the desired thickness of the deposit; and l. After the deposition is complete, the plasma is turned off and the deposit is quenched in vacuum by admitting cold Ar (cooled using a coil immersed into an alcohol and dry ice mixture coolant) into the deposition chamber.

At this point, the material, still on the mandrel, is removed from the vacuum deposition chamber and the copper mandrel is chemically removed. Additional post-deposition steps of surface finishing, cutting, etc. may be employed.

The device may be removed from the substrate after device formation by any of a variety of methods. For example, the substrate may be removed by chemical means, such as etching or dissolution, by ablation, by machining or by ultrasonic energy. Alternatively, a sacrificial layer of a material, such as copper, or nickel, may be deposited intermediate the substrate and the nitinol tube or the device formed there from. The device may be formed while the nitinol tube is still on the mandrel using laser cutting, laser ablation, or chemical or electrochemical etching with the use of a photolithographic pattern, or any similar methods. Then it maybe removed by melting of the sacrificial layer, selective chemical etching of the same, or using other suitable means.

The resulting device may then be subjected to post-deposition processing to modify the crystalline structure, such as by annealing, or to modify the surface topography and composition, such as by cleaning and passivation.

Figure 3:
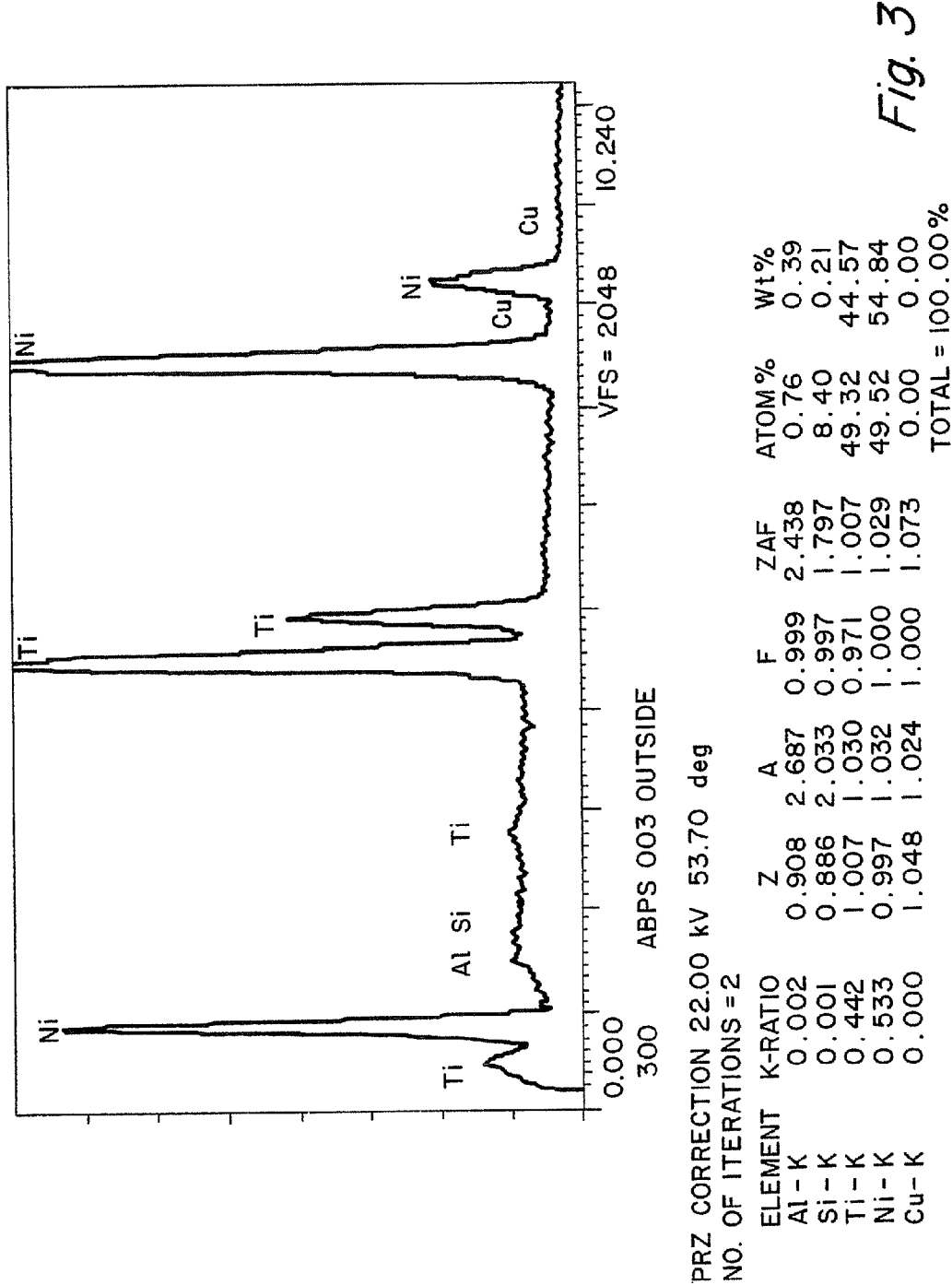
FIG. 3 is an electron microprobe spectrum of the inventive nitinol film deposited by sputter deposition.

FIG. 3 is electron microprobe spectrum of the inventive nitinol film deposited by sputter deposition in accordance with the method of the present invention. The spectrum was obtained on the outside surface of a 6.35 mm sputter deposited nitinol tube. Measurement was taken using energy dispersive spectroscopy (EDS). The data demonstrates that the film is a pure, stoichiometric nitinol. The presence of trace amounts of aluminum and silicon is attributed to surface contamination. X-ray diffraction analysis of the same material confirmed 100% crystallinity of the nitinol film.

Figure 4:
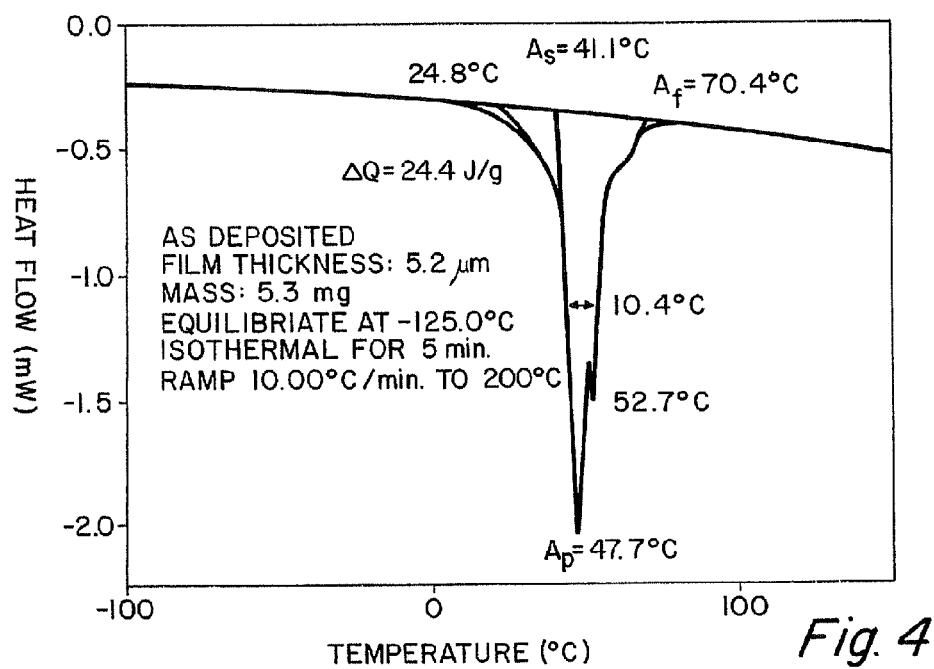
FIG. 4 is a Differential Scanning Calorimeter curve obtained from testing the inventive nitinol film.
Figure 5:
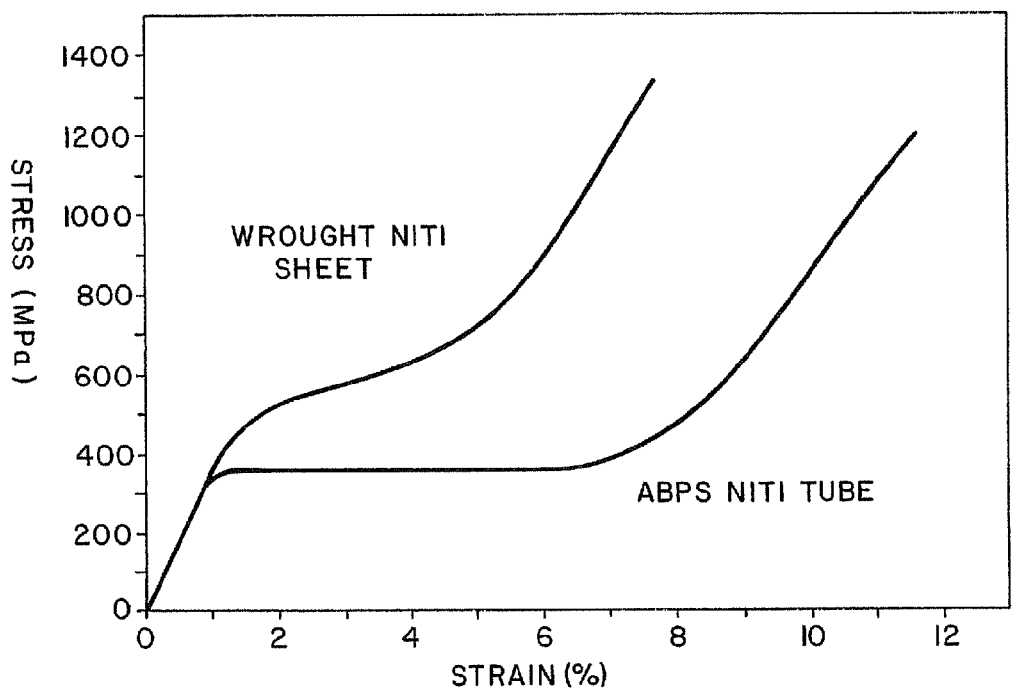
FIG. 5 is a graph depicting the stress-strain curve characteristic of the inventive nitinol film.

FIG. 4 is a graph illustrating testing by differential scanning calorimetry (DSC) of the inventive film produced by the inventive method. The DSC curve demonstrates a robust transition exhibiting a high ΔH value of 24.4 J/g. The results of testing the inventive high-strength nitinol film using dynamic mechanical analysis (DMA) are set forth in FIG. 5. FIG. 5 is the stress-strain curves for the inventive nitinol film, Curve A, and a wrought nitinol sheet, Curve B. The wrought nitinol sheet was thinned by chemical etching to achieve a thickness of about 10 μm suitable for testing on the DMA instrument. The inventive nitinol film A broke at the highest stress and strain depicted on the graph, thus, the ultimate stress was approximately 1250 MPa, while the ultimate strain was about 12%. The results shown in FIGS. 4 and 5 were obtained on the same film. The wrought nitinol film did not break, but testing reached the load limit of the DMA instrument at approximately 1400 MPa and a strain limit of about 7.5%.

Figure 6A:
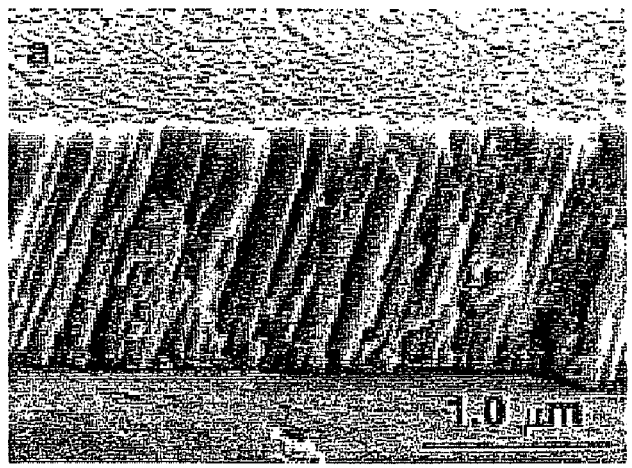
FIG. 6 is a scanning electron micrograph depicting a transverse cross-sectional view of a conventional (6A) and the inventive (6B) nitinol film.
Figure 6B:
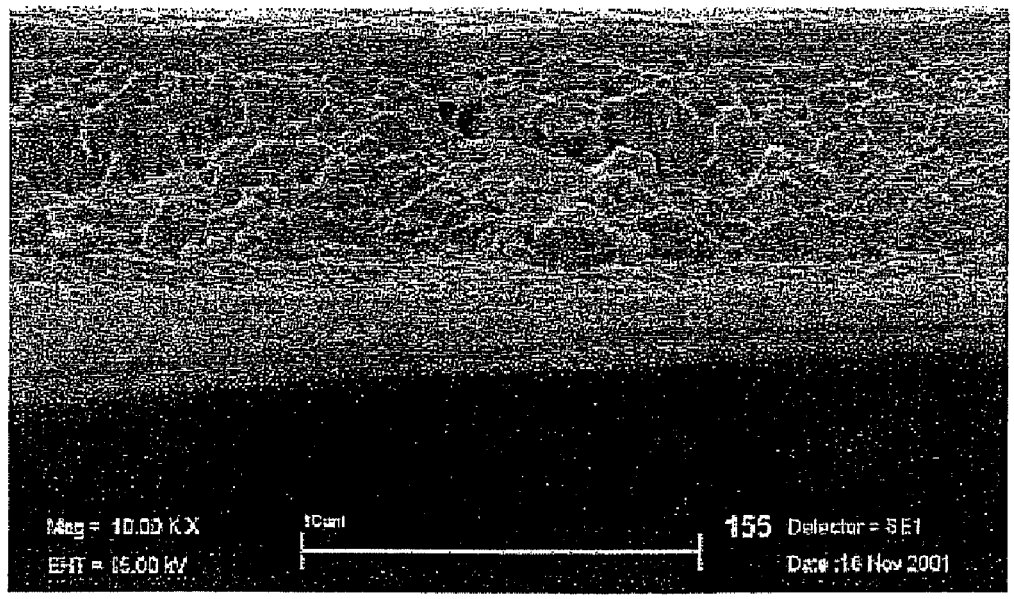

FIG. 6A is a scanning electron micrograph of a prior art sputter deposited nitinol film (a transverse cross-section of a 5 μm thick sample of the inventive nitinol film taken at 10,000× magnification. FIG. 6A illustrates the microstructure morphology of conventionally sputter deposited nitinol film (Chu, J. P., et al. *Deposition and characterization of TiNi-base thin films by sputtering, Materials Science and Engineering,* A 277 (1-2) (2000) pp. 11-17) which is characterized by having a generally columnar texture of the film. FIG. 6B is a fractured transverse cross-sectional scanning electron micrograph of a section of an inventive 5 μm film. It is readily apparent that the inventive film exhibits a complete absence of columnar morphology and is characterized by a grain structure which exhibits close compaction and virtually no surface roughness.

Figure 7:
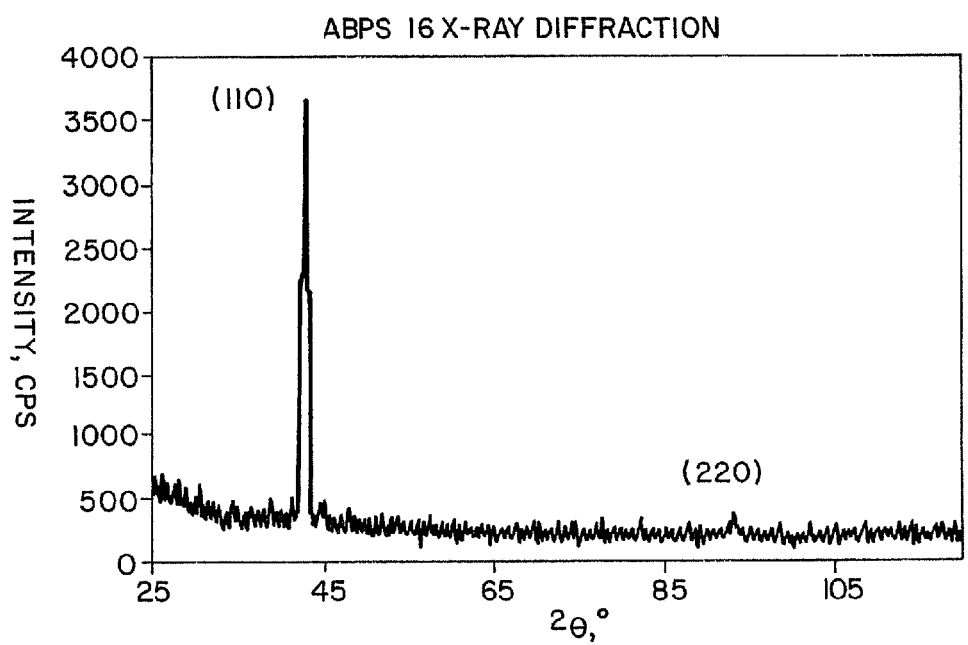
FIG. 7 is an X-ray diffraction pattern of the inventive nitinol film.

FIG. 7 is an x-ray diffraction graph of a 5 μm sample of the inventive nitinol material. The strong peak of approximately 3600 cps intensity at about 438 on the 2θ axis, without the presence of any other significant peaks is clearly indicative of the absence of precipitates in the inventive nitinol material.

Figure 8:
FIG. 8 is a transmission electron micrograph obtained from the inventive nitinol film.

FIG. 8 is a transmission electron micrograph taken on the same 5 μm sample of inventive nitinol material used for the x-ray diffraction depicted in FIG. 7. The micrograph verifies that the average grain size for the inventive nitinol material is about 0.1μ.

Figure 9:
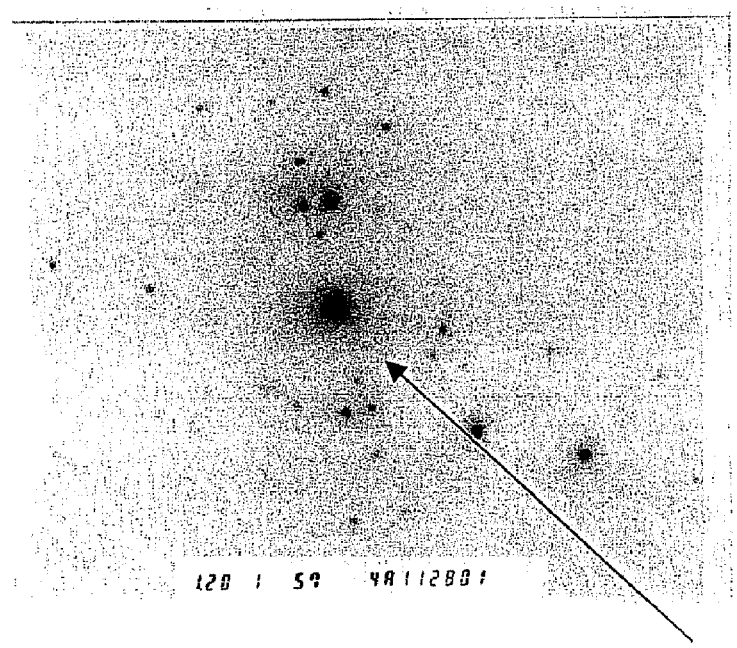
FIG. 9 is an electron diffraction pattern obtained from the inventive nitinol film.

FIG. 9 is an electron diffractogram taken on the same 5 μm sample of inventive nitinol as depicted in FIGS. 7 and 8, and depicts a virtually complete absence of precipitates. There is a very faint trace of a $Ti_3Ni_4$ present, however, there is no evidence of other precipitates in the diffractogram.

Figure 10:
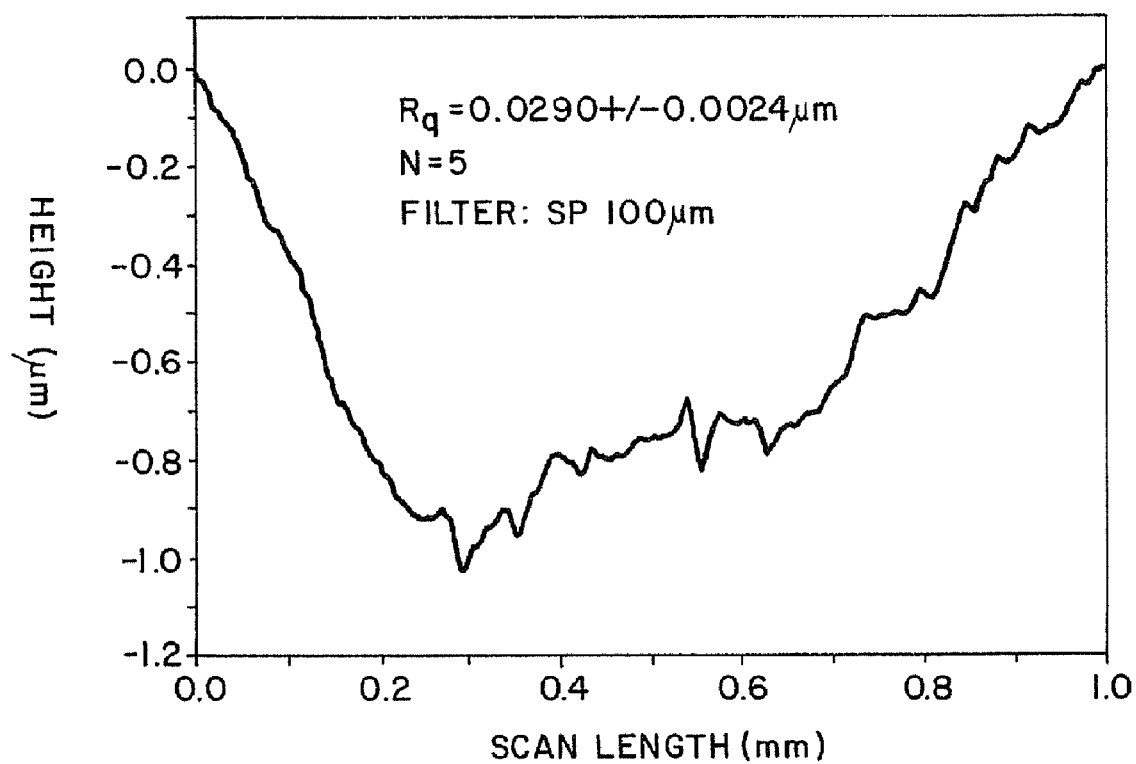
FIG. 10 is a surface profilometer track obtained from testing the inventive nitinol film.

FIG. 10 is a surface scan using surface profilometry taken on the luminal surface of an inventive nitinol material formed as a cylindrical tube. The low surface roughness of the deposited material is the result of the smoothness of the substrate and is determined by the nature and extent of pre-deposition substrate polishing and surface preparation.

Figure 12:
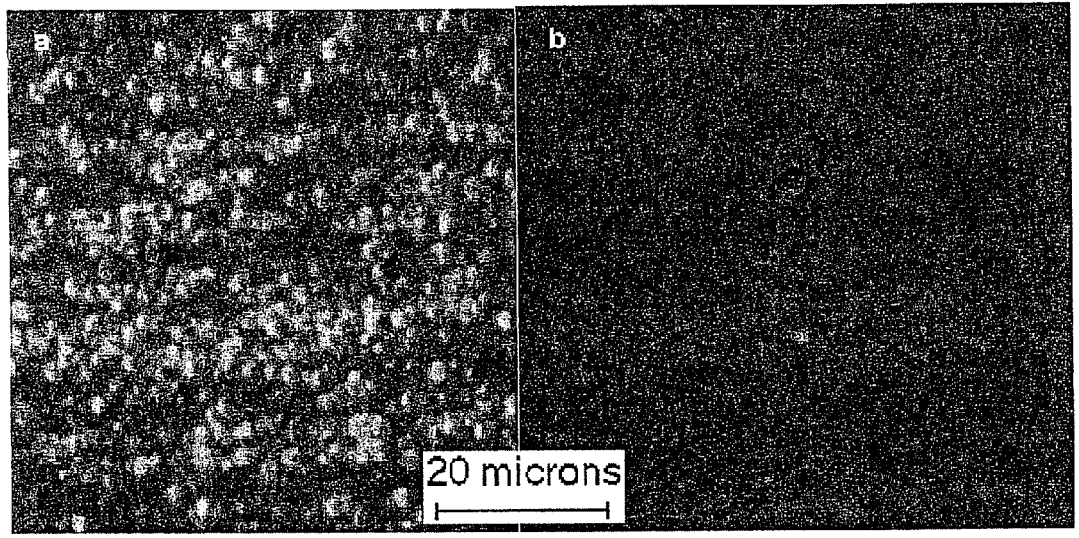
FIG. 12 (Section a) is a dark field optical micrograph taken through a 100× objective of a 5 μm nitinol film grown under conditions where energetic particles from the target were excluded from the substrate.
Figure 13:
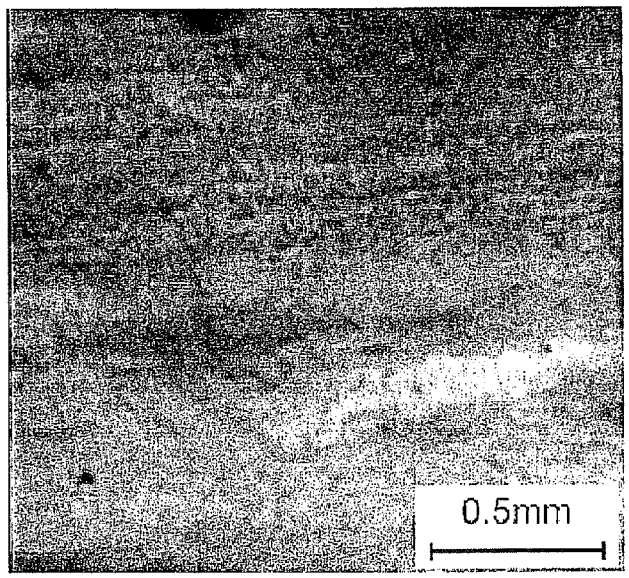
FIG. 13 is bright field optical micrograph taken through a 4× objective of a 5 μm nitinol film depicting both rough and smooth regions on the surface of the film.

FIG. 12 and FIG. 13 are optical micrographs in dark field (FIGS. 12A and 12B) and bright field (FIG. 13) microscopy illustrating a more gross view of the outside surface of the inventive material. In FIG. 12 (Section a), the surface of a 5 μm nitinol film having substantial surface roughness which is obtained where energetic particles are excluded from the substrate. Such a surface is characteristic of a columnar morphology depicted in FIG. 6A. In distinction to FIG. 12 (Section a), FIG. 12 (Section b) illustrates a substantially smoother outside surface where energetic particles are permitted to reach the substrate. Thus, the smoother surface profile of FIG. 12 (Section b), which is consistent with the inventive nitinol material, represents a more perfect nitinol material than that obtained using the conventional sputter deposition process methodology depicted in FIGS. 6A and 12 (Section a).

Gross characterization of the resulting post-deposition film may be performed to determine whether the nitinol film grew with a columnar grain structure or with a non-columnar grain structure. As illustrated in FIG. 13, there is a difference in the luster between films and fill regions having columnar texture and films with non-columnar grain morphology. When nitinol is grown with a columnar texture, the columns are typically 0.1-1 micron in diameter, which yields a resulting surface that is rough and scatters ambient light, resulting in a reduced surface luster. Where, however, the nitinol film has a non-columnar grain structure, the film surface is substantially smoother than films exhibiting columnar grain structures and ambient light is reflected, resulting in a high surface luster to the film. Thus, simple visual observation under ambient lighting is capable of distinguishing differences between the low luster of a film having a columnar texture and the high luster of a film having a non-columnar grain structure. Thus, as depicted in FIG. 13, regions of higher luster are regions having no columnar texture, whereas regions of lower luster are regions of columnar growth. This luster difference is, however, is not well expressed and is difficult to observe when the film thicknesses are less than about 1 micron.

Figure 14:
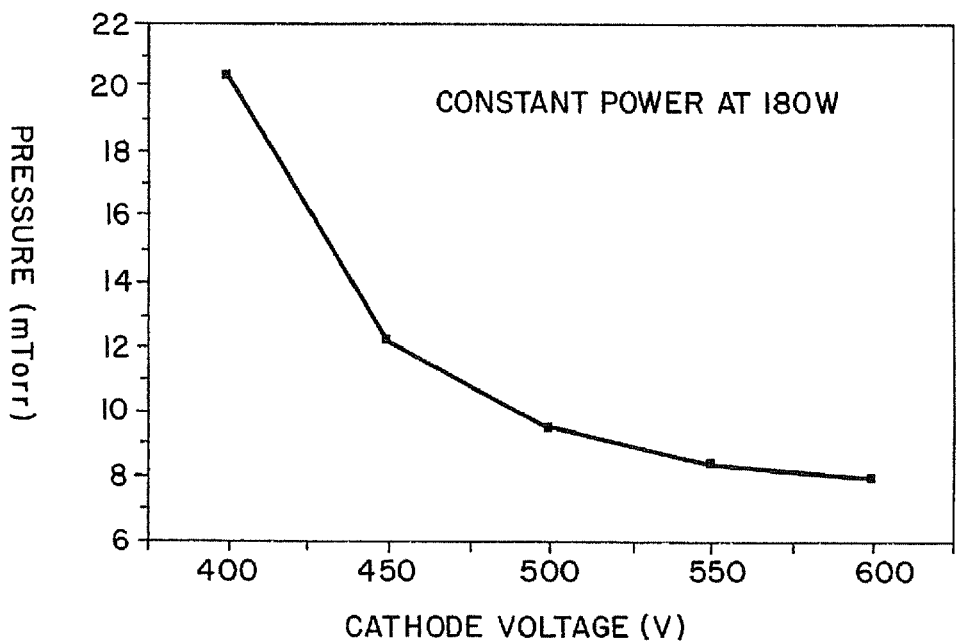
FIG. 14 is a graph depicting the relationship between cathode voltage and working gas pressure at constant sputtering power.
Figure 15:
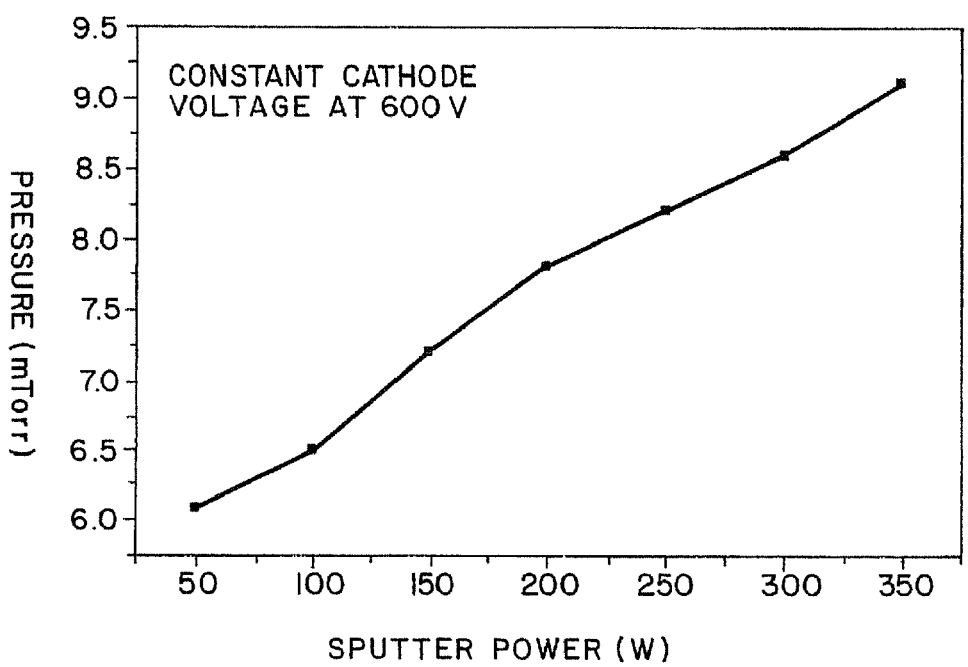
FIG. 15 is a graph depicting the relationship between working gas pressure and sputtering power for a constant cathode voltage.

FIGS. 14 and 15 illustrate the relationships between cathode voltage and working gas pressure at a constant sputtering power of 180 W (FIG. 14) and between sputtering power and working gas pressure at a constant cathode voltage of 600V (FIG. 15). It will be readily appreciated that there is a nearly inverse relationship between the cathode voltage and the working gas pressure at a constant sputtering power, and a nearly linear relationship between the working gas pressure and the sputtering power at a constant cathode voltage. It has been found that the particular values for cathode voltage, sputtering power and working gas pressure are dependent upon the particular magnetron geometry, magnetic field strength, configuration of the magnetic field and the vacuum system. Thus, the values expressed in FIGS. 14 and 15 are valid for the particular reactor system employed. Nevertheless, those proficient in the sputtering arts will recognize that the relationships expressed in FIGS. 14 and 15 are valid irrespective of the particular magnetron and reactor system utilized. In accordance with the present invention it is preferable to employ a cathode voltage between about 500-1000 V, preferably between about 600-900 V, in order to obtain the benefits of lower working gas pressures attendant to the this cathode voltage range.

It has been found that the inventive nitinol exhibits improved corrosion properties relative to conventional wrought nitinol tubing. A corrosion rate measurement was carried out by immersing a wrought nitinol tube (MINI-TUBES, France) and an inventive nitinol tube, of identical weight, in a 3M $H_2SO_4$+Methanol solution for 15 hrs at 37° C. Both the wrought nitinol tube and a deposited tube were treated by the same passivation procedure. The weights and surface areas of each tube were measured before and after exposure to the acid bath. From these measurements, corrosion rate data was calculated as 4.18 μg/cm$^2$/hour for the wrought material and 1.54 for the deposited tube. Thus, the inventive vacuum deposited nitinol material exhibited greater resistance to corrosion. Based upon this data and based upon the well-known relationships between corrosion and fatigue resistance, it is reasonable to conclude that the inventive vacuum deposited nitinol tubes would also exhibit improved fatigue resistance when compared to wrought nitinol materials.

Thus, in accordance with the present invention there is provided a vacuum deposition method for sputter depositing nitinol films having higher mechanical properties than those attainable or previously known in the art. The inventive vacuum deposition method entails controlling both the process parameters and the relationships between individual process parameters and depositing a nitinol film having high-strength mechanical properties. By carefully regulating the base pressure of the vacuum system, the quality and pressure of the process gas, the quality and finish of the substrate material, the temperature of the substrate, the power and voltage supplied to the cathode, the target material and material quality, the target surface temperature, and the throw distance, and balancing the relationships between these parameters, high-strength nitinol films having thicknesses between about 0.1 μm and 25 μm may be produced.

While the invention has been described with reference to its preferred embodiment, those of ordinary skill in the relevant arts will understand and appreciate that the present invention is not limited to the recited preferred embodiment, but that various modifications in substrate material selection, manner of controlling the substrate surface, deposition methodology, and deposition process parameters may be employed without departing from the invention, which is to be limited only by the claims appended hereto.

What is claimed is:

1. A method for fabricating nitinol film using a vacuum sputter deposition apparatus having a magnetron, a cathode, a cooling device thermally coupled to the cathode and a deposition chamber capable of being selectively isolated from the atmosphere, the method comprising the steps of:
   a. disposing at least one cylindrical target selected from the group consisting of nickel, titanium and nickel-titanium alloy in the deposition chamber;

b. disposing a cylindrical substrate that is spatially separated from and concentric with the cylindrical target in the deposition chamber;

c. supplying a working gas to the deposition chamber;

d. sputter depositing material from the at least one cylindrical target to form a substantially non-columnar crystalline film under conditions where the mean free path of the sputtered particles is greater than about half the distance between the cylindrical target and the cylindrical substrate;

e. removing the deposited material from the cylindrical substrate.

2. The method of claim 1, wherein step a. further comprises providing at least one nickel target and at least one titanium target.

3. The method of claim 1, wherein the cathode and the target are at least partially thermally isolated.

4. The method of claim 3, wherein the sputter deposition apparatus further comprises a thermally insulating ceramic material in insulating contact between the target and the cathode.

5. The method of claim 1, wherein at least a portion the substrate has a surface roughness with an $R_a$ value less than about 50 nm.

6. The method of claim 1, wherein the working gas in step c. is selected from the group consisting of He, Ne, Ar, Kr, and Xe.

7. The method of claim 1, wherein the substrate is heated to a temperature between about 400° C. to 550° C. prior to step d.

8. The method of claim 1, wherein step b. further comprises applying a bias voltage to the substrate.

9. The method of claim 8, wherein the bias voltage is a negative voltage.

10. The method of claim 9, wherein the bias voltage is less than or equal to about −120 V.

11. The method of claim 1, wherein step c. further comprises the step of admitting Ar gas into the vacuum deposition system to a pressure between about 0.1 to about 30 mTorr.

12. The method of claim 1, wherein step d. further comprises the step of positioning the deposition substrate and the target such that a throw distance between the deposition substrate and the target is less than about 25 mm.

13. The method of claim 1, wherein the cylindrical substrate is disposed along the central axis of the deposition chamber.

14. The method of claim 13, wherein step d. further comprises the step of rotating the substrate such that the deposited film is tubular in shape.

15. The method of claim 1, wherein step d. further comprises the step of quenching the deposited nitinol film within the sputtering apparatus.

16. The method of claim 1, further comprising the step of visually inspecting the deposited nitinol film and qualitatively determining surface roughness of the deposited nitinol film based upon the luster of the deposited nitinol film.

17. A method for fabricating nitinol film, comprising the steps of:

a. providing a vacuum deposition apparatus;

b. providing at least one cylindrical target selected from the group consisting of nickel, titanium, nickel-titanium alloy, nickel-titanium-X alloy wherein X is selected from the group consisting of copper, chromium, tantalum and zirconium;

c. providing and heating a cylindrical substrate disposed concentrically with the cylindrical target before and during a deposition run;

d. vacuum depositing nitinol metal from the at least one cylindrical target onto the cylindrical substrate to form a substantially non-columnar crystalline film;

e. controlling at least one vacuum deposition processing parameter selected from the group of isothermally heating the cylindrical target, controlling the base vacuum pressure, deoxygenating the working gas, controlling the deposition pressure, controlling surface roughness of the cylindrical substrate, controlling the composition of the cylindrical substrate, applying a negative bias voltage to the cylindrical substrate and controlling the throw distance between the cylindrical substrate and the cylindrical target;

f. removing the deposited nitinol film from the cylindrical substrate.

18. The nitinol film of claim 17, wherein the nitinol film has an ultimate strength of at least about 1000 MPa.

19. The nitinol film of claim 18, wherein the nitinol film has a maximum strain of at least about 10%.

20. A method for fabricating nitinol film comprising the steps of:

a. sputter depositing nitinol in a vacuum system having a magnetron, a cylindrical target, a cylindrical substrate disposed concentrically with the cylindrical target, a cooling device thermally coupled to a cathode and a deposition chamber capable of being selectively isolated from the atmosphere; and b. controlling the energy of particles emitted from the cylindrical target such that the mean free path of the emitted particles is greater than about one-half the throw distance between the cylindrical target and the cylindrical substrate.

* * * * *